United States Patent
Hoftman

[11] Patent Number: 6,035,852
[45] Date of Patent: Mar. 14, 2000

[54] INFLATED CUFF ANESTHESIA/RESPIRATOR MASK WITH IMPROVED NASAL/MAXILLA BONE ADAPTATION

[76] Inventor: Moshe Hoftman, 22205 Dardenne Ave., Calabasas, Calif. 91302

[21] Appl. No.: 08/947,291

[22] Filed: Oct. 8, 1997

Related U.S. Application Data

[63] Continuation-in-part of application No. 08/697,861, Aug. 30, 1996, Pat. No. 5,738,094.

[51] Int. Cl.$^7$ .................................................. A62B 18/08
[52] U.S. Cl. ............................... 128/206.26; 128/206.24; 128/206.21
[58] Field of Search ......................... 128/206.21, 206.23, 128/206.24, 206.26, 206.28

[56] References Cited

U.S. PATENT DOCUMENTS

| | | |
|---|---|---|
| D. 293,613 | 1/1988 | Wingler . |
| D. 323,908 | 2/1992 | Hollister et al. . |
| 790,057 | 5/1905 | Hively . |
| 1,206,405 | 1/1916 | Smith . |
| 1,287,149 | 12/1918 | Walter et al. . |
| 1,632,449 | 6/1927 | Mckesson . |
| 2,313,999 | 3/1943 | Kreiselman . |
| 2,435,721 | 2/1948 | Lehman . |
| 2,535,938 | 12/1950 | Lombard . |
| 2,625,155 | 1/1953 | Engelder . |
| 2,765,788 | 10/1956 | Raiche . |
| 2,875,757 | 3/1959 | Galleher et al. . |
| 3,042,035 | 7/1962 | Coanda . |
| 3,330,274 | 7/1967 | Bennett . |
| 3,982,532 | 9/1976 | Halldin et al. . |
| 4,062,357 | 12/1977 | Laerdal . |
| 4,201,205 | 5/1980 | Bartholomew . |
| 4,347,205 | 8/1982 | Stewart . |
| 4,384,577 | 5/1983 | Huber et al. . |
| 4,559,940 | 12/1985 | McGinnis . |
| 4,803,981 | 2/1989 | Vickery . |
| 4,905,686 | 3/1990 | Adams . |
| 4,913,401 | 4/1990 | Handke . |
| 5,121,745 | 6/1992 | Israel . |
| 5,738,094 | 4/1998 | Hoftman ............................ 128/206.26 |

OTHER PUBLICATIONS

"Understanding Anesthesia Equipment", Ja Dorsh et al, pp. 363–392 Williams : Wilkins, 1984.

Stedman's Medical Dictionary, 26 ed,, ed. Marjory Spraycar, ©1995, Williams : Wilkins, Baltimore, MD, 21201 USA.

Primary Examiner—Aaron J. Lewis

[57] ABSTRACT

The present invention is an inflatable cuff type anesthesia mask with three methods of improved support shell orientation of the inflatable cuff in combination with and to enable the successful operation of the mask at a point substantially more inferior on the bridge of the nose than currently shown in the prior art. In addition, the face directed inner edge of the support shell/cuff attachment forms a novel outline for improving the gas tight seal on the human face.

10 Claims, 8 Drawing Sheets

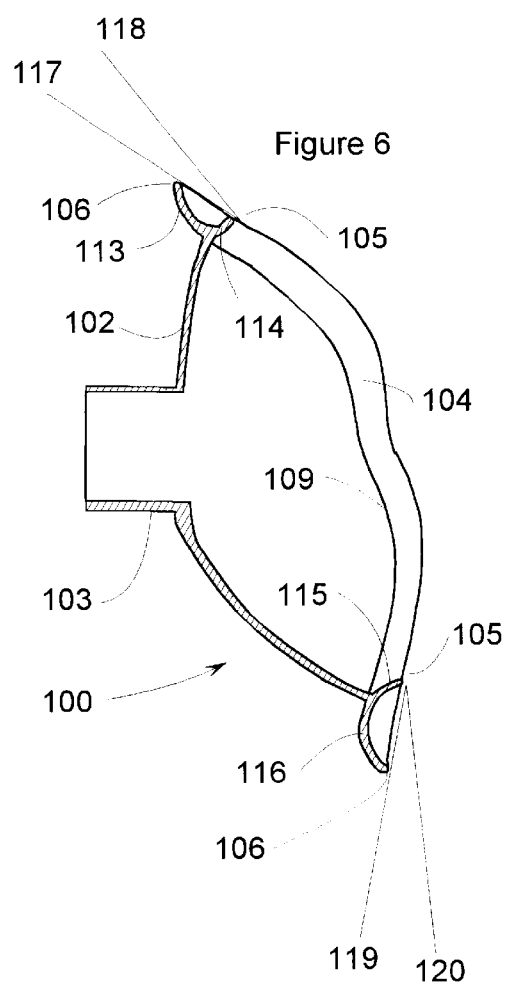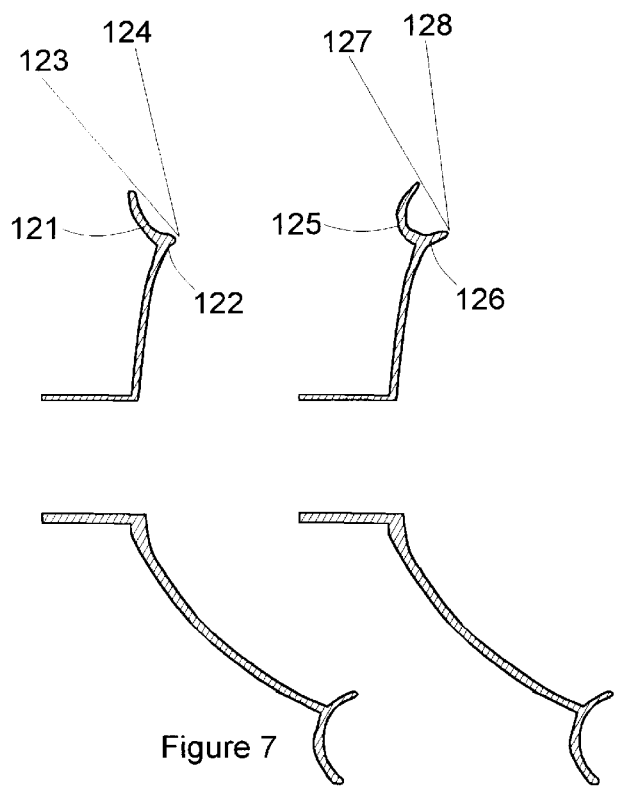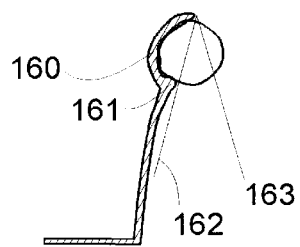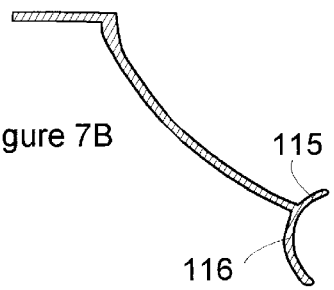

INFLATED CUFF ANESTHESIA/ RESPIRATOR MASK WITH IMPROVED NASAL/MAXILLA BONE ADAPTATION

This application is a continuation in part, under 35 USC 120, of U.S. Ser. No. 08/697,861 filed Aug. 30, 1996, and now U.S. Pat. No. 5,738,094.

BACKGROUND OF THE INVENTION

The present invention relates to anesthesia and respirator masks typically used in the medical arts The section of the book by J. A. Dorsch et al, pp. 363–392 of "Understanding Anesthesia Equipment" (Williams & Wilkins, 1984) describes several popular types of anesthesia masks. An important aspect of the anesthesia mask noted on page 363 is that of the two types of face seal "One is a cushion (rim pad) that is inflated with air or filled with a material that will conform to the face when pressure is applied. The second type of seal is a flange that is an extension of the body." Masks that can be widened or narrowed to fit the face are shown in FIG. 13.1 and 13.2 are a hybrid of the above two types. The interior void which is inflated and extends from the face seal section of their double rubber shell construction up to the connector orifice. This type of mask is in contrast to those inflatable masks whose inflatable portion is separate from the dome or semi-spherical external support shell necessary to connect a flexible inflatable cuff with the connector orifice.

In the Dorsch book, the Laerdal mask of FIG. 13.8 is an example of the single support shell/inflatable cuff mask. It is further noted on page 367 that "The best fit is obtained by selecting a mask and testing it before induction of anesthesia. The smallest mask that will do the job is the most desirable because it will cause the least increase in dead space, will usually be easiest to hold, and will be less likely to result in pressure on the eyes." The very serious implications of failing to obtain a gas tight seal between the gas delivery conduits and the face of the wearer has made each of the above factors the focus of specific improvements in the art. The problems associated with masks in the art are shown and described on pages 367–368, especially directed to FIG. 13.11. In that FIG. 13.11, the Laerdal mask is shown being held in place with one hand, the most common and desirable method since the anesthesiologist or nurse will then have one hand free to use for other tasks. It will readily occur to the skilled person that there is tremendous potential for a failure to maintain a gas tight seal about the patient's mouth and nose, especially in the cheek area as the masseter/buccinator muscles form a rather softer area for which the seal must be maintained. The single support shell/inflatable cuff mask is especially prone to this failing due to the lack of sensible response of the separation of the inflated cuff from the cheek. The second type of mask described above may more readily alert the anesthesiologist or nurse of a gas seal break or leak in the cheek area because the edges of the firm face seal flange do not extend substantially outwardly beyond the effective sealing edge to obscure the flange/skin seal. However, an unsymmetrical facial bone structure or musculature of the patient or a failure to maintain a relatively narrow range of downward orientation of the non-inflatable cuff mask makes the flange type of mask more difficult to maintain in a gas tight seal than the mask with an inflatable cuff.

U.S. Pat. No. 790,057 shows an early inhaler anesthesia mask. A generally inward curvature is seen in FIG. 2 showing an adaptation for the bridge of the nose of a patient.

U.S. Pat. No. 1,206,045 shows a nasal inhaler with a hard, gas tight support shell with "flange" or plastic material to be situated between the shell and the patient as sealing means.

U.S. Pat. No. 2,313,999 generally shows a double shelled mask similar to that of FIG. 13.1 of the Dorsch book. The double shell comprises generally quite firm but flexible rubber and extends from the seal to the gas conduit at the orifice connector to the variable diameter expanded section at the face-contacting portion of the double shell. In contrast to the Laerdal mask shown in the Dorsch book downward pressure on the supports shell generally presses the "flange" face contact surface in a direction outward from the axis formed by the orifice connector. In another aspect of this outward motion of the sealing surface of the "flanges" of the non-inflatable cuff type mask, the skin of the patient is drawn away from the nose and mouth. The opposing action of reacting skin and musculature improves the pressure of and increases surface area of the sealing contact surface area between the mask and the patient.

U.S. Pat. Nos. 2,535,938, 2,625,155, 2,765,788 and 3,042,035 generally show masks with relatively hard "flange" material. So although downward pressure tends to increase the seal by causing a reaction of opposing skin and muscles, the relatively narrow "flange" material almost eliminates this advantage and, for the face with extensive wrinkling in old age, will tend to "trap" the creases in the skin between the harder "flange" material and permit gas to flow between the atmosphere into the mask or vice versa.

U.S. Pat. No. 2,875,757 describes an inflatable cuff type mask. FIG. 3 very clearly shows the cuff cross-section. FIG. 4 shows how the inflated cuff looks and presents an inward facing sealing surface. In a cross section of the mask through an axis formed through the axis of the orifice of the orifice connector, it is seen that the support shell outwardly and away from the orifice connector and over the inflatable cuff such that the bottom most extended surface of the inflated cuff extends only slightly beyond the rim of the support shell. Downward pressure on the outside of the mask to form a seal with the patient's face necessitates the inflated cuff be pressed inward. The greatest pressure that may be applied to such a mask is limited to that pressure within which the cuff will maintain a clearance between the patient's face and the hard support shell.

U.S. Pat. No. 3,982,532 shows another double shell mask construction where the void formed extends from the face contact surface to the orifice connector. With careful choice of materials and with regard to relative flexibility and curvature "memory", certain embodiments of the device in this patent may, upon downward pressure of the mask to the face of a patient, may move outwardly from the nose and mouth the skin and facial muscles.

U.S. Pat. No. 4,062,357 generally shows the Laerdal mask described above. It will be seen from FIGS. 3, 6, 7 and 8 that downward pressure application to the face of a patient will cause the inflated cuff to assume a generally elliptical cross-section whereby increasing downward pressure causes the ends of the ellipse to move roughly both inward, toward the axis of the general angle of the downward pressure, and outward, away from that axis and away from the patient's nose and mouth. The result of the relatively equal inward and outward force distribution on the inflated cuff is that almost only about half of the downward pressure is transmitted to an outward motion of the cuff to facilitate a reaction of the skin and muscle back toward the nose and mouth. This is an inherent disability since the skin and musculature extending from the contact surface of the inflated cuff to the nose and mouth of the patient are generally less reactive and somewhat more elastic in that direction than in the other direction.

U.S. Pat. No. 4,201,205 shows an oxygen mask with a single firm-flexible clear plastic shell with a "flange" for improving the seal between the wearer's face and the mask. This simple construction is consistent with the limited seal needed.

U.S. Pat. No. 4,347,205 shows an inflated cuff filled with a dual lumen.

U.S. Pat. No. 4,559,940 shows an inflatable chamber for occluding a patient's mouth during airway intubation.

U.S. Pat. No. 4,803,981 shows a nose inhaler comprising only a rather firm rubber foam material. Downward pressure would tend to, as with similar "flange" type masks, move skin and muscles away from the nose.

U.S. Pat. No. 4,913,401 discloses a valve assembly generally representative of inflating valves for inflatable cuffs.

U.S. Pat. No. 5,121,745 shows a collapsible inflatable cuff mask with equal-force distribution similar to that of the above Laerdal mask.

U.S. Design Pat. No. D293,613 show an inflatable cuff type mask with inflating valve located at the nose bridge area.

U.S. Design Pat. No. D323,908 show an inflatable cuff type mask with an extension of the support shell to be, in operation, located just superior to the bridge of the nose, and providing the middle finger of the anesthesiologist or nurse with improved support.

There is a need to provide an inflatable cuff type mask wherein the benefits of the "flange" type mask may be obtained while also obtaining the increased surface contact area provided by the inflatable cuff type masks.

SUMMARY OF THE INVENTION

The present invention is an inflatable cuff type anesthesia mask with two primary methods of improved support shell orientation of the inflatable cuff in combination with and to enable the successful operation of the mask at a point substantially more inferior on the bridge of the nose than currently shown in the prior art. These improved orientations may be used separately or, more preferably, together. The first of the improved orientations is an outward chamfering of the outer edge of the support shell to such that the subsequent attachment of an inflatable cuff to the support shell and placement of the mask on the face of a patient necessarily forces substantially the greatest portion of the cross-section of the inflated cuff away from the nose and mouth of the patient. As shown in the Figures and described below, the angle of the cuff attachment means of the support shell is roughly preferably about 5–45 degrees elevated from the sealingly effective surface of the face where the inflated cuff will be depressed to form a gas tight seal. This outward chamfering is at least applied about the arch formed by the nose down to about the first contact with the face above the zygomatic bone. The chamfered extension of the support shell is most preferably applied about the entire peripheral outer edge of the support shell, obtaining the dual benefit of improved gas tight sealing from counter reaction from outwardly pushed skin and having only a single support shell to simplify manufacturing and reduce costs. More than one shell may be used in connection with the present invention, i.e., some masks have obtained various gas mixing and introduction results with more than one shell between the face and the atmosphere. However, only one support shell is needed to effect the objects of the present invention.

The second outward chamfering effect of the inflatable cuff of the present invention is to form the cuff such that downward pressure on the mask to the face of the patient causes substantially all of the deformation of the cross-section of the cuff beyond the outer rim of attachment means to the support shell. Although this special formation of the cuff is advantageous when used alone, it is more advantageous when used with the outward chamfering of the outer edge of the support shell. It is highly beneficial when both chamfering orientations are applied about the entire outer edge of the support shell of the mask whereby the medial anterior length of the facial surface covered by the mask is significantly reduced by moving the contacting/sealing surface of the inflatable cuff from a more superior to a more inferior position on the bridge of the nose. The result of reducing that medial mask length reduces the total mask contact area, thus reduces the dead space in the mask by 10–20% or more over a prior art mask with a relatively longer facial medial length.

In addition, the parison of the inflatable cuff is blow-molded, roto-molded or vinyl dipped to effect a gluing section on a substantially thicker upper or superior surface of the inflatable cuff while the remaining cuff surface comprises a relatively thin and pliable (and optionally and preferably "tacky" or slightly sticky) expandable material. This results in a far more rugged construction so that the additional stresses on the cuff of pressing the skin of the wearer outward may be made without concern for rupturing the cuff.

Thus, the outward chamfered inflatable cuff creates an opportunity to effectively and more efficiently maintain a gas tight seal over a higher arch of the nose than taught by the prior art. The mask to face sealing surface is thus withdrawn to a sufficient distance from the infraorbital arch such that even quite heavy application pressure will not result in corneal abrasion or pressure on the eye. It is within the art to provide a pre-inflated cuff or to provide a valve through which air or gas can be injected, preferably with a syringe. It is another embodiment of the present invention to provide the inflatable cuff with a dual valve whereby application of pressure between the thumb and forefinger will cause inflation of the cuff to a desired pressure, an especially advantageous feature since sustained pressure of the mask on the patient may potentially tend to cause deflation of the cuff.

In a further embodiment of the present invention, it has been found that, in contrast to any prior art mask, whether single or double shelled, a most preferred embodiment of the chin and cheek portions of the cuff and/or outer edge of the support shell are adapted to be outwardly chamfered while the nasal bridge section, from the bridge of the nose to the maxilla, is adapted such that the effective application angle of the cuff and/or outer edge of the support shell compared to the sealing surface portion of the face is parallel or just slightly inwardly chamfered. For relatively firm application of the mask or where the cuff would tend to press above the infraorbital arch and thus into the eyelid, the parallel or slightly inwardly chamfered support shell or cuff permits adaptation to the widest range of facial curvature in the three named regions, i.e. nasal bridge, cheek (referred to later as the transition section) and chin referred to later as the mandible section).

Two further improvements in the prior art are found in the mask of the present invention. Two additional inventive aspects of that mask are (1) the face directed edges of the inflatable cuff support closest to the glued or molded connection seam or zone connecting that support to the support shell define an innermost support outline for the inflatable cuff, whereby a superior universal facial seal with the inflated cuff is obtained, and (2) a support shell complementing the facial seal is made with a minimum of dead space by defining an upper plane at an apex of the support shell, preferably surrounding the hose connection conduit, at a minimum distance from the lips and nose of the wearer and extending the support shell down to the connection to the innermost support outline for the inflatable cuff support. The problems in the prior art devices with inflatable cuffs relate mainly to inadequate seal to a wearer's face since the range of facial shapes is so broad. The prior art devices with a support shell and inflatable cuff are many times simply discarded at the point of use in favor of the masks formed with bulky, face enveloping rubber masks as shown in the Dorsch et al reference on page 364 as the Connell Mask. The flexible dual rubber walls can be pressed on the face of a patient effectively covering the entire front of the face, over the anterior portion of the zygomatic arch and pressing against the eyes, to obtain an adequate seal. This prevents viewing of the breathing response of the patient or accumulation of moisture or other fluid.

The prior art support shells for use with inflatable cuffs are routinely made with a support shell face directed outline, to which the inflatable cuff support is attached, that forms a single plane. Adaptation to the user's face is made by making various configurations of the inflatable cuff, as shown in U.S. Pat. D323,908. Such inflatable cuff adaptation is ineffective to "fill in" gaps on the wide variety of human face shapes, just as a pillow only effectively blocks breathing when it is spread across the entire face. It has been unexplored in the prior art to find the most effective adaptation of the support shell face directed outline to successfully create a support for the inflated cuff seal for the many forms of human faces with respect to age, health, injury and inherited characteristics.

The present invention requires formation of the support shell face directed outline into at least two to four "directional planes" symmetrical about a top view midline of the support shell and roughly forming two trapezoidal, middle planes and two curved end planes in angled relationship to each other at curved transition vertices. The use of at least four directional planes produces the most effective inflatable cuff support with the least design effort. When a support shell face directed outline is combined with the invention support shell formed as a curved, downward extension of an upper directional plane comprising an apical portion of the shell, the amount of dead space is minimized since it need not be adapted for extreme downward pushing on the inflatable cuff to fit the patient face.

BRIEF DESCRIPTION OF THE DRAWINGS

FIGS. 6, 7 and 7A are cutaway side views of the mask of the present invention without the inflatable cuff.

FIG. 7B is a cutaway side view of the of the mask of the present invention with an inflated inflatable cuff shown for the nasal bridge section alone.

FIG. 12 shows the planes together at vertices lines and FIG. 13 shows them separated at those lines.

DETAILED DESCRIPTION OF THE INVENTION

The technology disclosed below improves the art of inflatable cuffs for respirator or anesthesia masks The present invention will be discussed with reference to the above Figures. In the Figures, many aspects of the present invention are referred to with the same aspect item numbers in the several Figures. The use of identical item numbers indicates that the aspect identified in one Figure has substantially the features of the same aspect in another Figure. The use of several views with substantially the same aspects has been necessary to better describe the present invention.

Figure 1:
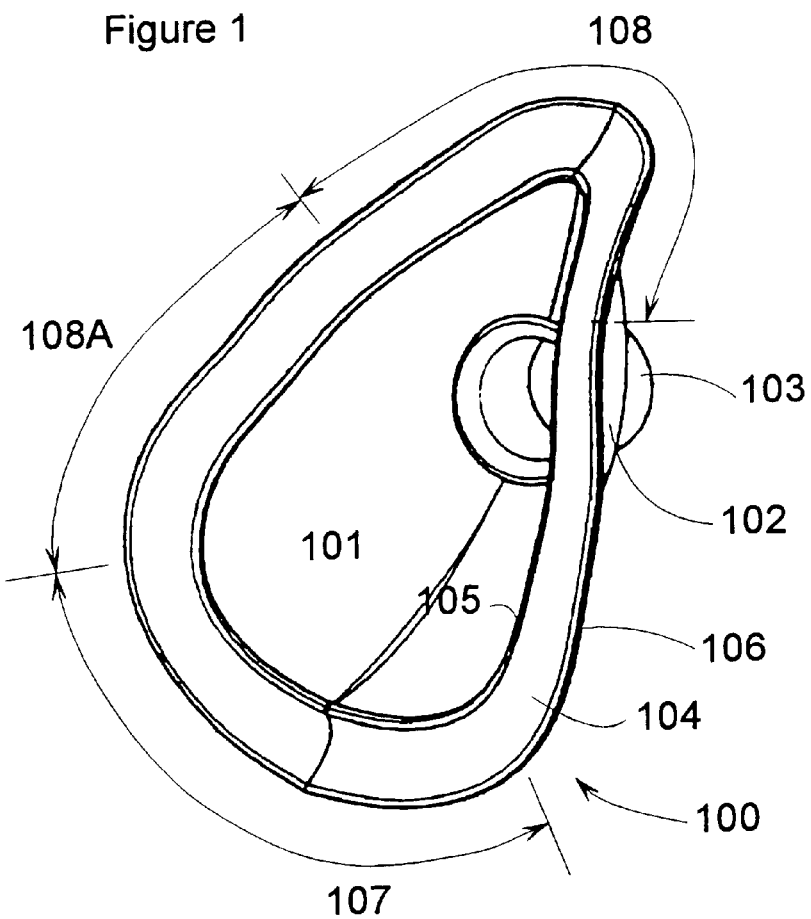
FIG. 1 is a rear view of the mask of the present invention without the inflatable cuff. The rear view is angled sufficiently to the right of rear so that the view is roughly parallel to the right side of the support shell when viewed from the rear.

FIG. 1 shows the mask of the present invention without the inflatable cuff. This is true for all the Figures except for the nasal bridge section shown in FIG. 7b, FIGS. 8, 9, 9A and 10 so that the novel orientation and dimensions of the mask of the present invention might be clearly shown. FIG. 1 shows a mask 100 with a support shell with inside surface 101 and outside surface 102. Hose connector 103 is molded integrally with or glued or later applied to the connector orifice at the base of hose connector 103. Cuff attachment means 104 extend from the outer edge of the support shell with an inner edge 105 and an outer edge 106.

Figure 3:
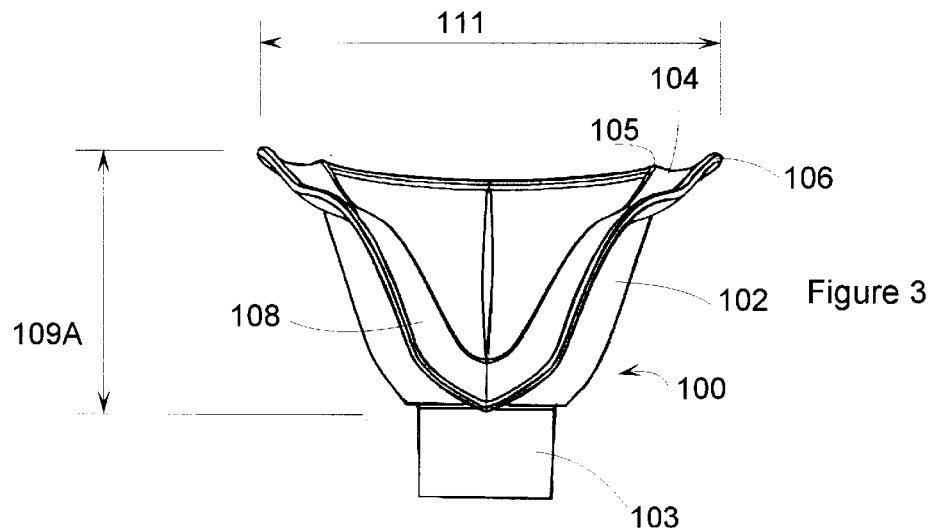
FIG. 3 is a top view of the mask of the present invention without the inflatable cuff.
Figure 8:
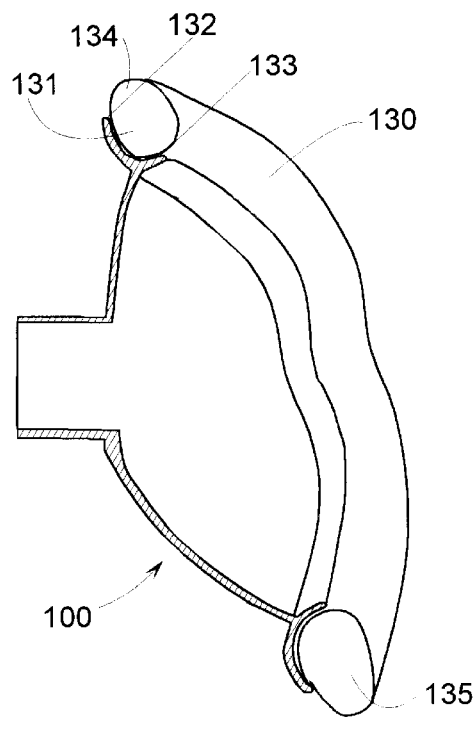
FIGS. 8, 9 and 9A are cutaway side views of the of the mask of the present invention with an inflated inflatable cuff.

Operationally defined sections are shown in FIG. 1 to indicate sections of cuff attachment means 104 whose chamfering of the cuff attachment means 104 and cross-sectional shaping of the inflatable cuff in that section may be independent of the other sections to obtain a beneficial result for widely different facial types or desired gas seal pressures. Mandible section 107 preferably is adapted to be oriented at the lower section of or just below the inferior portion of the orbicularis oris muscle below the mouth, although it may also be adapted to be located as low as the chin of the patient. Nasal bridge section 108 preferably is adapted to be oriented at its topmost edge above the highest medial facial prominence or the most inferior external extension of the nasal bone, thereafter extending the mask down the sides of the nose bridge to the maxilla in the most direct fashion such that the length of the mask contacting surface on the nose is minimized. Transition section 108A defines the sealing section of the mask generally from the edge of the maxilla in an inferior or downward direction away from the nose but below the zygomatic bone so that the mask preferably need not be formed to seal the very difficult zygomatic to maxilla transition below the infraorbital arch. This transition section in prior art masks has not been adapted to the facial contours of the patient. The attachment ridge of the support shells in the prior art all define a relatively straight line in side view from the mandible section to the nasal bridge section. In the prior art, there has been no substantial outward flaring of the support shell in the transition or cheek section to reduce downward pressure necessary to "fill in" the cheek with the inflatable cuff, as seen in FIGS. 3, 6, and 8 of U.S. Pat. No. 4,062,357 and U.S. Design Pat. Nos. D293,613 and D323,908.

An inflatable cuff disposed along the operationally defined sections 107, 108 and 108A will thus advantageously "fill in" or more fully occupy the region between the medially directed ending of the infraorbital arch and the prominating maxilla and nasal bones. There will be no need at the most extreme pressure of the anesthesiologist or nurse at the highest downward pressure on the mask to press the upper edge of the mask over the infraorbital arch into the eye socket. An increasing downward mask pressure on the mask of the present invention will be translated into a force to move outwardly the inflated cuff in sections 108 and 108A and tend to even more effectively press the eyelids together to improve eye protection during anesthesia. The medial length of mask 100 from the midpoint of section 107 to the midpoint of section 108 is referred to herein as the nose bridge to lower orbicularis oris muscle distance and defines an effective mask length not previously used in the art. The reduction of this distance reduces the total facial surface area enclosed by mask 100 and thus also reduces dead or void space between the inside surface 101 and the face of the patient, reducing the dilution effect of gas transfer from the connecting hoses to the airway to the lungs of the patient.

Figure 2:
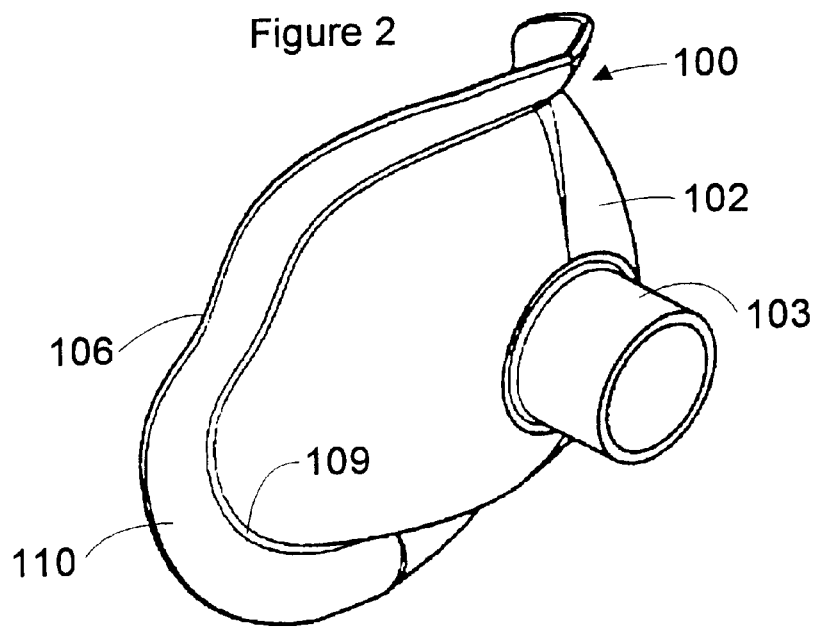
FIG. 2 is a front view of the mask of the present invention without the inflatable cuff. This front view is angled sufficiently to the left of front so that the view is roughly parallel to the right side of the support shell when viewed from the front.

FIG. 2 shows many of the features of FIG. 1, however the cuff attachment means upper surface 110 and cuff attachment means—support shell connection 109 are shown. The connection between the support shell and the cuff attachment means may be formed by integrally molding or later gluing or other effective connection that will support heavy downward pressure as is typical for application of anesthesia masks. It is this connection that in part defines an outwardly chamfering angle for the cuff attachment means 104 in the various operationally defined sections. The parabolic, roughly circular or roughly flat cross-sectional shapes that may be effectively used for the cuff attachment means also contribute to the outward chamfering of the cuff attachment means.

FIG. 3 shows the mask of the present invention from above so that width 111 and effective height 109A can be seen. Minimizing these dimensions reduces dead space in the mask 100, although the wide variety of facial dimensions and curvatures require that several models be available to the user. Nasal bridge section 108 in FIG. 3 is seen prominently outwardly chamfered, although the degree of chamfering, as described later, is in part operationally defined so that adaptation to the facial curvature of different persons will effect a desired and preferable angle between the translated force direction of downward application pressure and the facial surface to which the inflatable cuff is applied.

Figure 4:
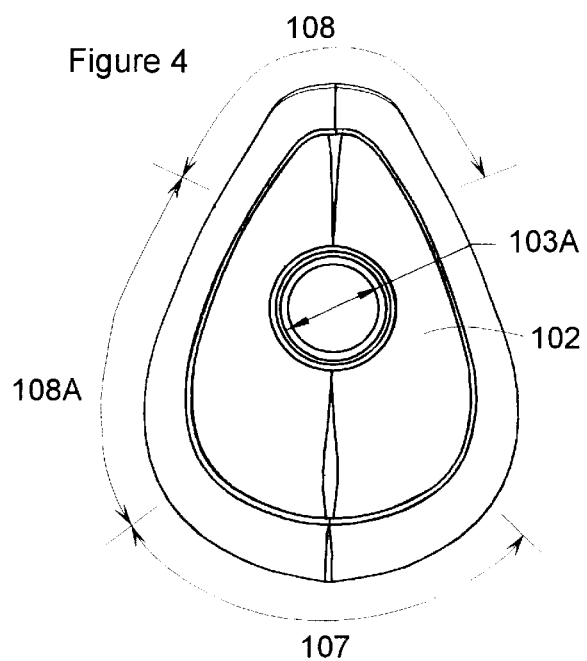
FIG. 4 is a front view of the mask of the present invention without the inflatable cuff.
Figure 5:
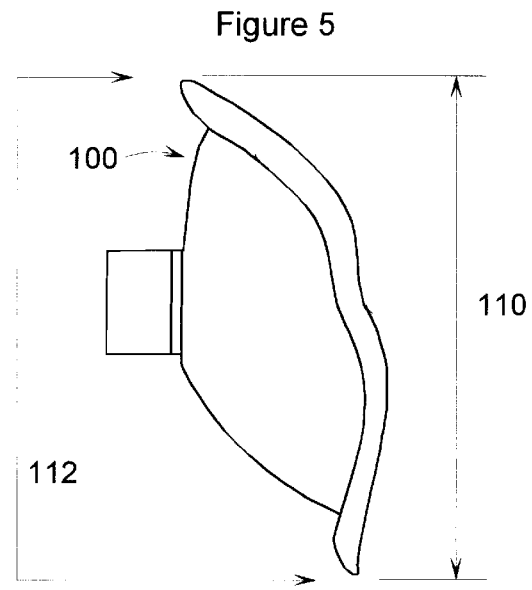
FIG. 5 is a side view of the mask of the present invention without the inflatable cuff.

FIG. 4 shows the mask of the present invention in a front view with the diameter of the hose connector 103A defined. FIG. 5 shows a side view of the mask of the present invention with a height 110 defined by the extreme outer edges of the cuff attachment means. Medial section line 112 defines the cross-section of mask 100 for the rest of the Figures and also indicates the direction of force typically applied by medical personnel to obtain a sealing contact between the face of a patient and the mask. This force application can be seen in FIG. 13.11 of the Dorsch book. However, because operational definitions are so important to obtaining the objects of the present invention, it is known and easily observable that the direction of force applied by medical personnel on such masks is widely variable with different pressures and downward (toward the face of the patient) directions being obtainable. It is the intention of the present invention to provide chamfering that is generally effectively at an angle upwardly outward and non-parallel to the facial sealing surface of the patient, although, for this embodiment wherein the outward chamfering is supplied in the nasal bridge section, it is only critical that the nasal bridge section 108 need be provided with such chamfering. Additional benefits of the present invention are described herein for providing chamfering of the cuff attachment means in sections 107 and 108A.

FIG. 6 shows a medial cross section of the mask of the present invention, showing cuff attachment means 104 such that its medial cross-sectional shapes in sections 108 and 107 are also shown, although sections 108 and 107 are not shown in their entirety as in FIG. 6. Cross-sectional shapes for sections 107 and 108 have outer cuff retaining extensions 113 and 116 respectively and inner cuff retaining extensions 114 and 115 respectively. The extreme ends of the inner and outer cuff retaining extensions generally define upward and outward chamfering directions 117 and 119. Downward pressure typically applied to the outer surface 102 by medical personnel will cause that force to be translated into a downward and outward force generally normal to the directions 117 and 119, which directions are non-parallel to facial surface directions 118 and 120 respectively. The acute angles formed by the intersection of the facial surface directions and the upward and outward directions is preferably about from 4–45 degrees, and more preferably from about 5–15 degrees. This force translation moves the attached cuff in an outward direction with respect to the nose and mouth. Another advantage of such movement is that the patient with severe wrinkling or fascia weakening such as occurs following a burn recovery will be gently spread outwardly and the wrinkles will not be trapped beneath the equal pressure cuff of the Laerdal mask. FIGS. 7 and 7A show alternate configurations of the nasal bridge section cuff attachment means. In FIG. 7, a generally minimal directioning cuff attachment means is shown with a short inner cuff retaining extension 122 and outer cuff retaining extension 121 defining direction 123 against facial surface direction 124. In FIG. 7A, a highly directioning cuff attachment means is shown with a long inner cuff retaining extension 126 and outer cuff retaining extension 125 defining chamfering direction 127 against facial surface direction 128.

In contrast to the nasal bridge sections of the above specific embodiments, FIG. 7B shows a nasal bridge section cross-section wherein the effective application or sealing surface of the inflatable cuff is parallel or slightly inwardly chamfered comparison to the sealing surface of the face, while the transition section and the mandible sections are outwardly chamfered as described in the embodiments above. In FIG. 7B, a generally minimal directioning cuff attachment means is shown with a short inner cuff retaining extension 161 and outer cuff retaining extension 160 defining direction 162 against facial surface direction 163. The angle formed by directions 162 and 163 are preferably from about 0 to 15 degrees to permit quite heavy pressure on the nasal bridge section while preventing abrading or impressing contact of the support shell with the surface of the patient's skin. In this embodiment, adapting the cuff attachment means and/or the cuff to provide effective outward chamfering of the cuff in the transition and mandible sections combine the advantage of low application pressure in those sections to effect a gas tight seal with the option of providing high application pressure to the nasal bridge section where it is expected that greater variation in elevation and breadth of the nose will sometimes require greater application pressure.

Figure 9:
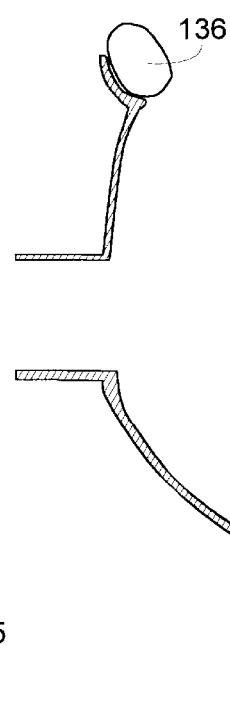
Figure 9A:
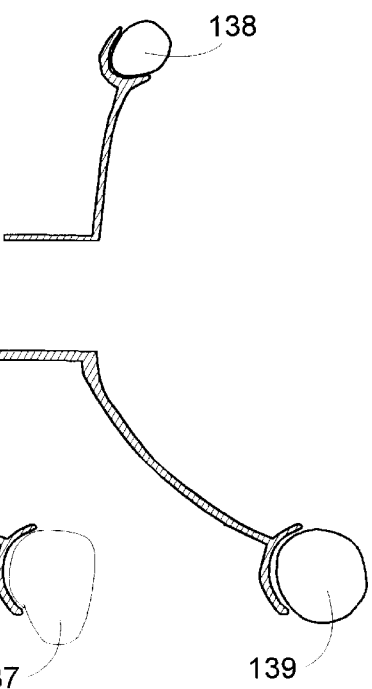

FIGS. 8, 9 and 9A show application of the several inflatable cuff cross-sectional shapes effective for obtaining the advantages of the present invention as applied to the embodiments shown in FIGS. 6, 7 and 7A. The inflatable cuff shapes 131, 135, 136, 137, 138 and 139 in the Figures indicate the many forms from circular to oblong that will be effective, however, generally the most effective shapes will have little or no inwardly lateral extension of the shape beyond the limit 133 while extending as much as 50% or more of the cross-sectional area in an outwardly lateral position past limit 132.

Figure 10:
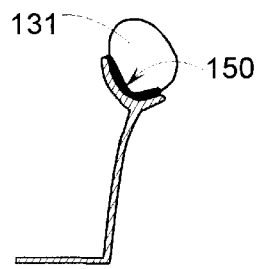
FIG. 10 is a cutaway side view of only the top half of the mask of the present invention for the purpose of showing thickness enhanced inflatable cuff with an improved surface for attachment of the inflatable cuff to the support shell.

FIG. 10 shows the thicker section 150 of inflatable cuff shape 131. Thicker section 150 is formed when blow molding the inflatable cuff on a superior surface and thereby forming a strong gluing surface. In another embodiment of the present invention, a valve and inlet tube a provided through upper surface 102 to the interior of the inflatable cuff. The inlet tube is provided with a dual valve arrangement whereby a connector tube between the valve may be pressed with the human hand and thereby expelling air into the cuff through the proximal valve and having the distal valve seal against connector tube pressure.

It is yet another embodiment of the present invention to supply upward extensions of the upper surface 102, such as the one shown in FIGS. 2, 3, 5 and 6 of U.S. Design Pat. No. D323,908 (which disclosure is incorporated herein) adapted for the digits of hand of the medical personnel applying the mask of the present invention. Specifically, two extensions of the upper surface 102 are preferably adapted to be located just above the nose and mouth of a patient, such as in the location of the thumb and forefinger of the medical personnel shown in FIG. 13.11 of the Dorsch book. These are referred to herein as finger grips, permitting relatively independent pressures of application to the nasal bridge and mandible sections. Another embodiment of the present invention uses a soft, pliable synthetic foam to fill the inflatable cuff.

The support shell of the present invention may be very stiff, semi-rigid or firm and may be formed from transparent or opaque materials, although transparent, semi-rigid polymer is preferred such that the medical personnel responsible for monitoring the patient may easily view the seal formed by the chamfering of either the cuff attachment means or the inflatable cuff. In addition, it is preferred in some situations to provide the support shell with strap means whereby adjustable straps may be joined to the support shell upper surface and drawn to the back of the head and/or neck of the patient. FIG. 9 of U.S. Pat. No. 4,062,357 shows generally such plurality of upper surface extensions adapted to retain adjustable straps.

It is a further embodiment of the present invention to provide the adjustable straps with an end section for releasable and adjustable attachment to the support shell comprising a "bead and string" arrangement. The "bead and string" arrangement comprises a length preferably from about 2–12 inches whereby a polymer or equivalent material is formed with short, narrow diameter "string" sections between shorter, larger diameter "bead" sections. The support shell strap attachment comprises an extension in which is formed a hole larger in diameter than the "bead", through which the "bead and string" length may be easily passed. Another hole in the support shell strap attachment is formed laterally and in communication with the first "bead" hole, although the diameter of this second hole and the first hole lateral communication therewith are between that of the "bead" and the "string" sections. Thereby a low cost and easily latchable and unlatchable means are provided for securing the mask of the present invention without constant pressure of human hands.

Figure 11:
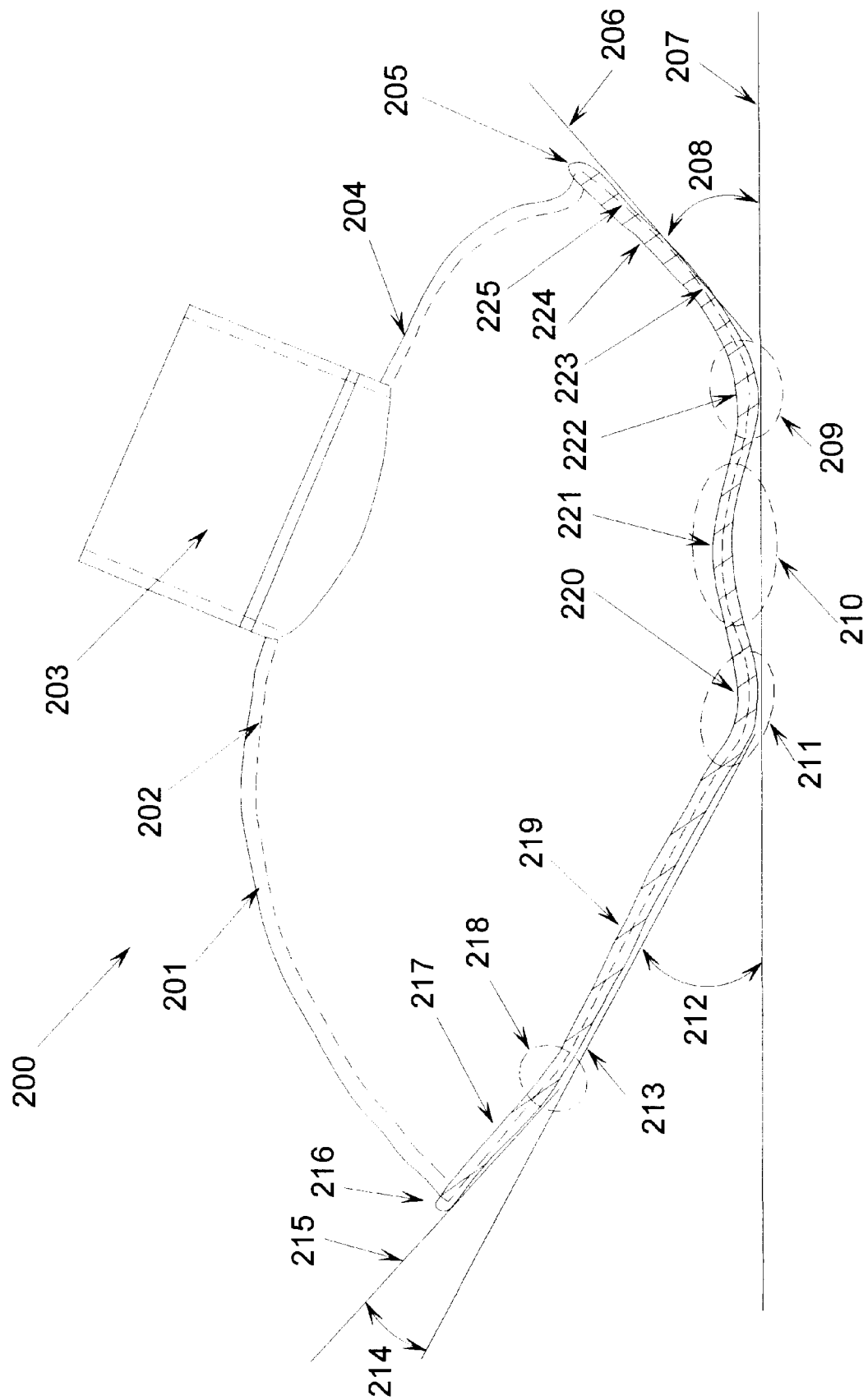
FIG. 11 is a more detailed side view of the mask of the present invention as substantially shown in FIG. 5. The inflatable cuff support attachment is cut away close to its gluing or molding seam connection to the support shell. Four "directional planes", defined by the face directed edges of the inflatable cuff support, are shown in edge view. The directional planes are shown connected at curved transition vertices in angled relationships to form the entire face directed edges of the inflatable cuff support.

Detailed Description of the Invention for Improvements Relating to Support Shell Face Directed Outline and Upper Directional Plane FIG. 11 is a more detailed side view of the mask 200, substantially shown in FIG. 5. The inflatable cuff support is cut away close to its gluing or molding seam connection 225 to the support shell 201. Four directional planes 217, 219, 221 and 224, generally for the chin, cheek, nasal/maxilla depression, and nasal bridge sections respectively, are defined by the face directed edges of the inflatable cuff support. In FIG. 11, those directional planes are shown in edge view. The directional planes are shown connected at curved transition vertices 218, 211 and 209 for planes 217/219, 219/221 and 221/224 respectively. Plane extensions 215, 213, 207 and 206 are shown for planes 217, 219, 221 and 224 respectively so that the relational angles can be appreciated. Angle 214 between planes 217 and 219 is preferably about 1–6 degrees, but most preferably about 3–5 degrees. Angle 212 between planes 221 and 219 is preferably about 35–45 degrees, but most preferably about 39–41 degrees. Angle 208 between planes 221 and 224 is preferably about 20–40 degrees, but most preferably about 29–31 degrees. Vertices 218, 211 and 209 are preferably generally curved instead of pointed to facilitate molding and a smooth surface for application of the inflatable cuff.

Figure 14:
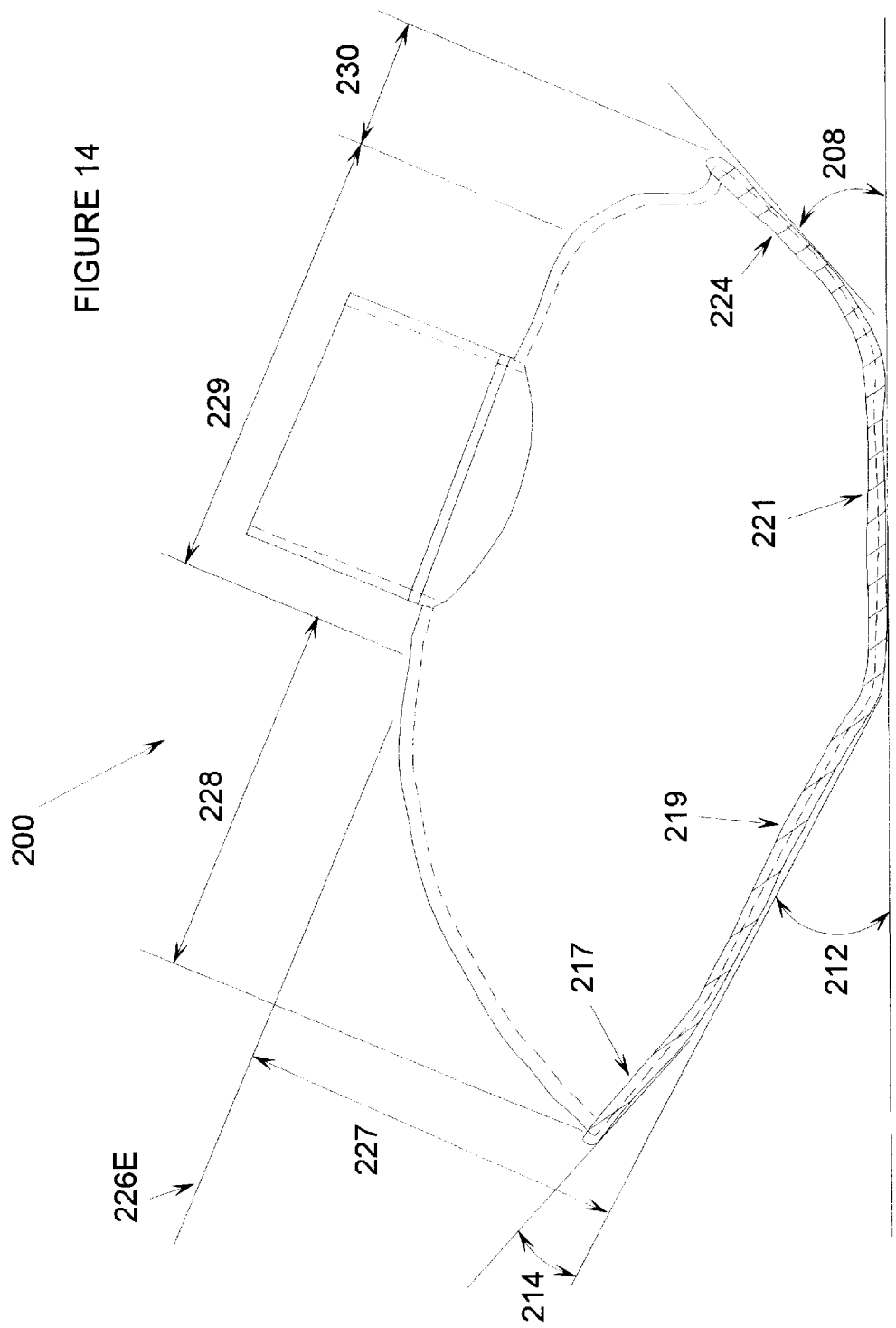
FIG. 14 is mask of FIG. 11 with definition and dimensioning of an upper directional plane about the hose connection and parallel to one of the other directional planes of the face directed edges of the inflatable cuff support.

A transition section 210 is preferably upwardly indented, as opposed to another flat embodiment of that aspect shown in FIG. 14. It has been found that this indentation of about 1–4 mm is more effective in adapting the inflatable cuff to seal the difficult nasal/maxilla indentation formed by the medially directed end portion of the infraorbital arch of the maxilla and the lateral, anterior directed facial edge of the nasal bone. It is this short, "valley" zone of the facial skeletal structure that varies so much between individuals and is additionally is at least partly filled with fascia, fat and few muscles of varying thickness and firmness. The present combination of at least planes 224 and 221 in the face directed outline of the support shell of a support shell/inflatable cuff mask overcomes that sealing problem.

In FIG. 11, hose connection 203 is located in an apical portion of the support shell 201. The thickness of a partly flexible, transparent support shell 201 is shown by the broken line of interior surface 202 showing a medial line of the interior surface. In one embodiment that thickness is about 2 mm. A nasal bridge section end 205 is shown for face directed outline of the support shell 201, as well as a chin section end 216 for the chin section. These ends will define certain dimensions for orientation of an upper directional plane, as defined below.

Figure 12:
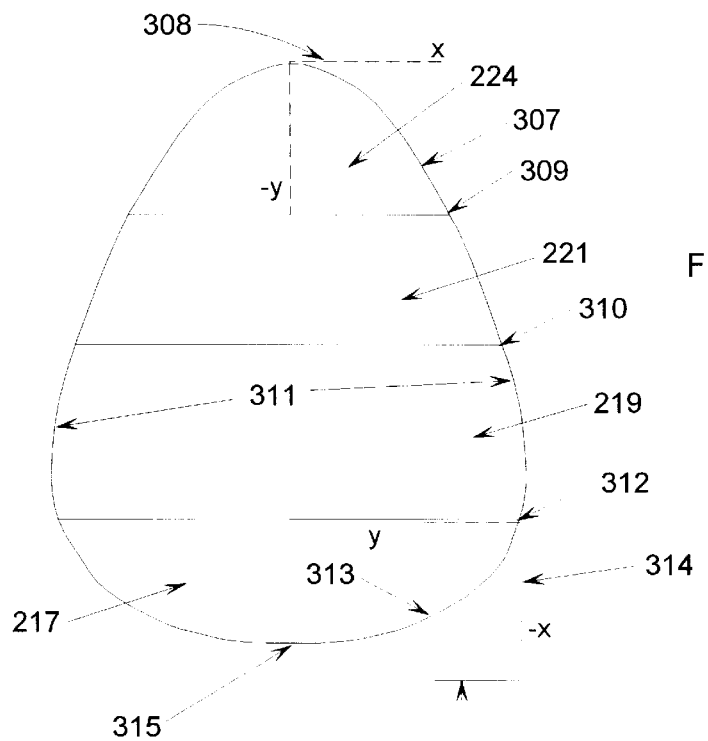
FIGS. 12 and 13 show the four directional planes in plan view.
Figure 13:
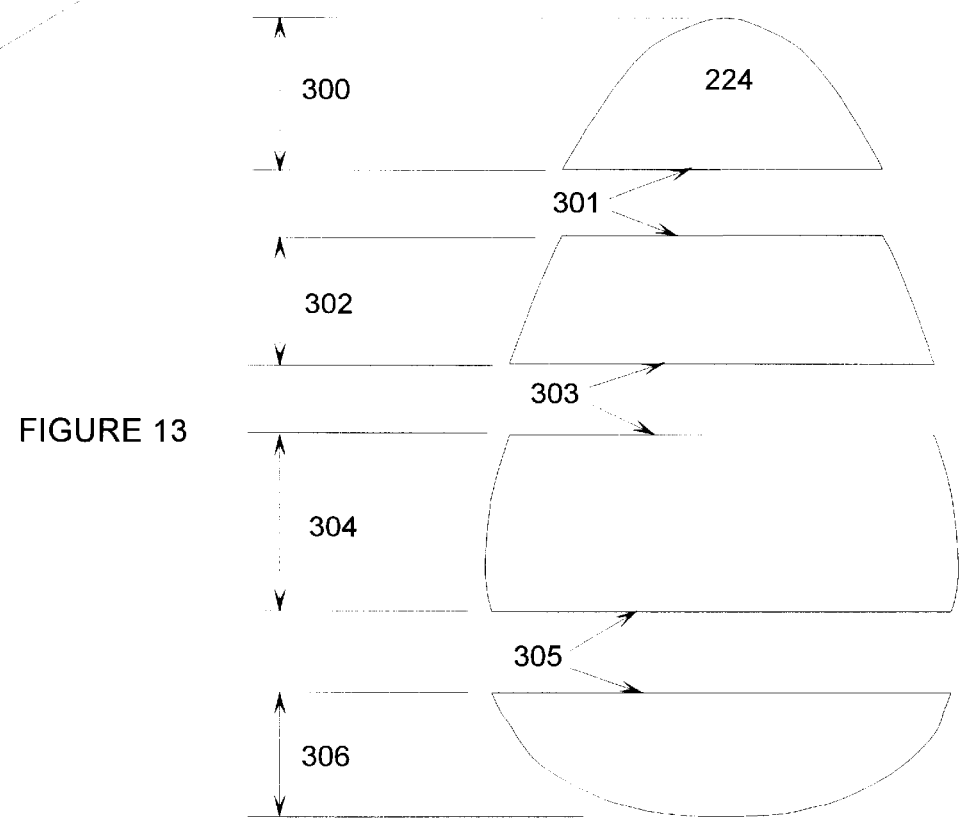

The plan views and dimensions of planes 217, 219, 221 and 224 are shown in FIGS. 12 and 13. A set of preferred dimensions and configurations for those planes follows.

For plane 217, height 306 is preferably about 20–22 mm, although may range from about 15–35 mm. A set of positive "y" and negative "x" axes 314 are shown with reference to a medial half 313 of the form of the curve of plane 217. Although generally a curved transition from one end of vertex 312 to a medial mid point, medial half 313 is typical of the form of the curve of the equation $y=-(\frac{1}{8}) x^3$ as plotted on axes 314. Vertex 305 is preferably about 69–71 mm, although may range from 50–80 mm.

For plane 224, height 300 is preferably about 25–27 mm, although may range from about 21–31 mm. A set of negative "y" and positive "x" axes 308 are shown with reference to a medial half 307 of the form of the curve of plane 217. Although generally a curved transition from one end of vertex 309 to a medial mid point, medial half 307 is typical of the form of the curve of the equation $y=-(\frac{1}{4})x^2$ as plotted on axes 308. Vertex 309 is preferably about 44–46 mm, although may range from 40–65 mm.

Plane 221 is generally a trapezoid symmetrical about the medial line for the other planes. Vertex 310 is preferably about 63–65 mm, although may range from 50–75 mm. Height 302 is preferably about 19–21 mm, although may range from about 15–30 mm. The lateral edges of plane 221 are substantially straight in plan view, although in a side view show the variation of transition 210 of FIGS. 11 and 14.

Plane 219 is generally a trapezoid or rectangle, preferably with slightly rounded or curved lateral edges 311 and symmetrical about the medial line for the other planes. The lateral edges of plane 221 are substantially straight in plan view, although in a side view show the variation of transition 210 of FIGS. 11 and 14.

It will be appreciated the planes 217, 219, 221 and 224 are flat in a preferred embodiment. The skilled person will appreciate that slight curvature of one or more of these planes due to manufacturing or other defects or design modifications may still obtain the benefits of the present invention. When preferably fabricated, the support shell 200 of the present invention can, surprisingly, create a gas tight seal on the face of many persons even without benefit of the inflatable cuffs that will be preferably and sealingly connected to the inflatable cuff support which is in turn attached to the support shell.

It is a further improvement in the art to reduce the volume of gas space between interior surface of the support shell, inflatable cuff support and inflatable cuff of the mask of the present invention and the face of the wearer. The surprisingly and widely effective seal of the face directed outline of the inflatable cuff support of present invention eliminates the need to provide a large design volume of dead space in case substantial pressing is needed to perfect the seal between the mask and the wearer's face.

Figure 15:
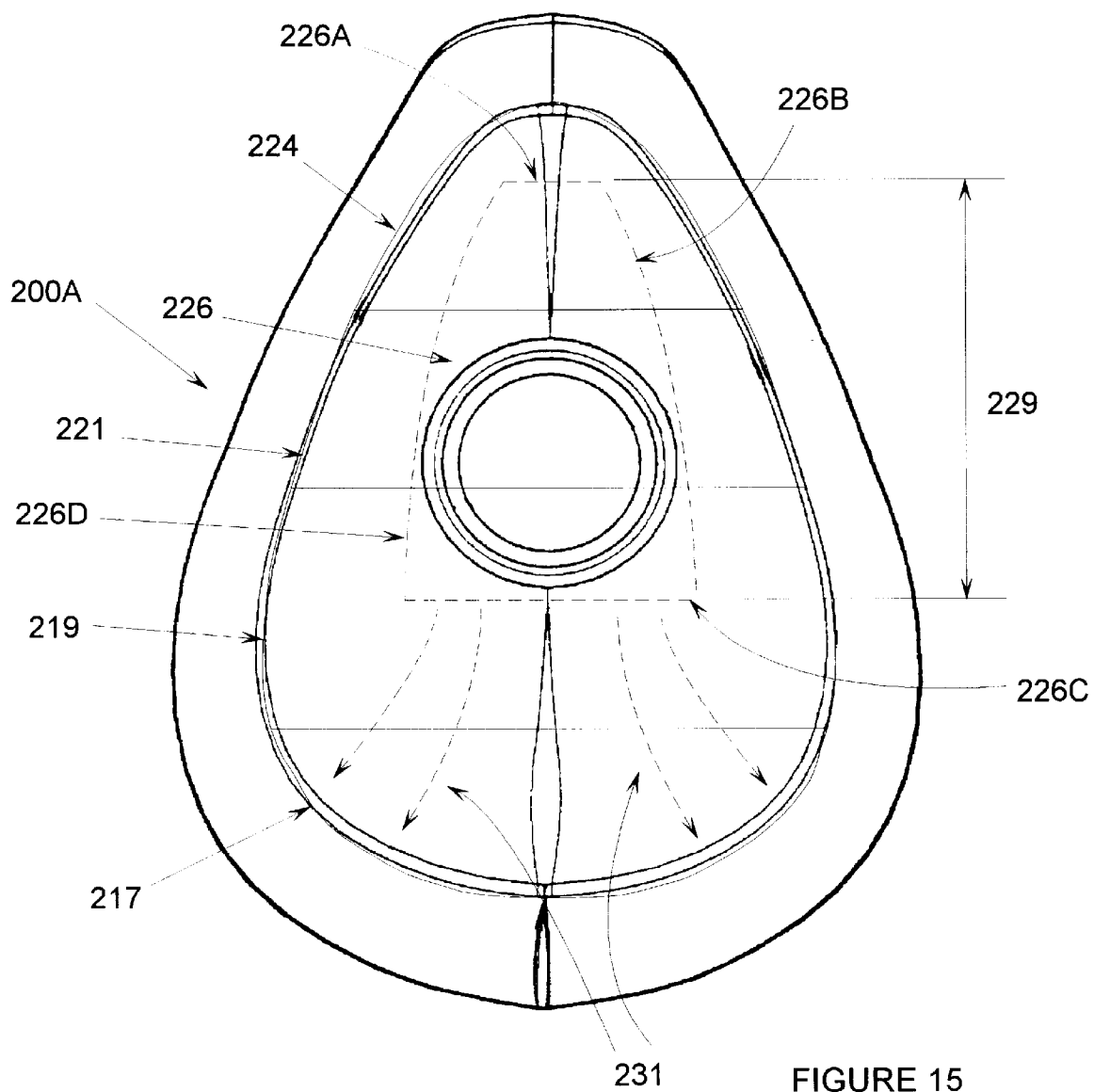
FIG. 15 is a plan view of the upper directional plane in a generally trapezoidal shape.

The mask 200 of FIG. 14 is also the mask of FIG. 11, although with dimensioning to show the position of an upper directional plane 226, defined by edges 226A–D shown in plan view in FIG. 15. Plane extension 226E shown in FIG. 14 shows that plane 226 is substantially parallel to plane 219 and located at a perpendicular distance 227 of about 37–43 mm from it, although the range may be from about 32–50 mm and still obtain substantial benefits of the configuration of the present invention. The plan view, medial line distance from edge 226C and end 216 is distance 228, is about 33–37 mm, although the range may be from about 31–45 mm and still obtain substantial benefits of the configuration of the present invention. The plan view, medial line distance from edge 226A and end 205 is distance 230, is about 4–7 mm, although the range may be from about 2–10 mm and still obtain substantial benefits of the configuration of the present invention. The plan view, medial line distance from edge 226A and edge 226C is distance 229, is about 36–43 mm, although the range may be from about 20–50 mm and still obtain substantial benefits of the configuration of the present invention.

Edges 226A and 226C are about 2–8 mm and 10–20 mm in length. The generally curved edges 226B and 226D are a preferred result of the effectively shortest length of a curved downward transition from plane 226 to the lateral or outside edges of planes 217, 219, 221 and 224. Molding techniques preferably produce a support shell interior surface which is smoothly concave with respect to the wearer, as shown in downward curved surfacing directions 231. A slightly outwardly curved form shown in FIGS. 11 and 14 are the most preferable form for the support shell transition section from the interior surface of the support shell with orientation and area with that of plane 226 and a face directed outline edge of the support shell 201.

It is one embodiment of the present invention to impose only planes 221 and 224 in their described relationship on the face directed outline edges of the inflatable cuff support 225. The rest of the outline could comprise an edge section of the same similar shape as that shown in FIG. 15 for support shell 200A (shown with inflatable cuff support intact, with no cut away sections) and which is generally upwardly curved in a side section view as shown in FIG. 5.

It is known to reduce by appropriate ratio medical devices for use with the pediatric or smaller patient. The devices for the mask described as the invention comprise those for the normal adult regardless of age, sex, race or other generally known genetic variation known for application of the present invention. It will be apparent that appropriate reduction by ratio in size and length but not in angled relation of the directional planes, will provide the pediatric or smaller patient with the benefits of the invention as described above. It will also be apparent upon inspection of the devices that the support shell is generally symmetrical about a plane normal to the directional planes and extending through a longitudinal medial line through ends 205 to 216. Thus, the side view of the mask of the present invention provides an edge view of the directional planes.

The present invention should provide at least directional plane orientation for the nasal bridge section and the nasal/maxilla transition section of the effective bottom edge of the support shell to obtain substantial directional gas tight sealing of the support shell/inflatable cuff mask to a patient's face. The present invention is distinguishes over the prior art especially in that the inflatable cuffs of the prior art were improved with substantial increases in inflated volume or difficult to manufacture face/inflated cuff curvature for a cuff that attached to a substantially flat plane bottom edge of the support shell. The orientation of the upper plane in a mask without a third directional plane as described above, i.e., one that is of obvious design in light of the above teaching for the first and second directional planes, is obtained with reference to the angled relationship of the second and third directional planes, whereby the third directional plane will be merely an imaginary reference plane for effective location of the upper plane.

The design options of the present invention will sometimes present the designer with considerable and wide ranges from which to choose appropriate modifications for the above embodiments. However, the objects of the present invention will still be obtained by the skilled person applying such design options in an appropriate manner.

I claim:

1. A respirator or anesthesia mask for a normal adult comprising:
   (a) an inflatable cuff;
   (b) a support shell with an interior surface adapted to be directed to the face of a patient;
   (c) cuff attachment means that sealingly interpose between and secure the inflatable cuff to the support shell at a lower edge of the support shell;
   (d) a face directed outline edge adapted to comprise an innermost support edge of the cuff attachment means, where such outline edge is symmetrical about a longitudinal medial line plane of the mask;
   (e) the outline edge forming defining edges of at least two planar shapes perpendicular to the longitudinal medial line plane, a first plane in a nose bridge section and a second plane in a nasal/maxilla section, the first plane and second plane having a first vertex joining them in angled relation to each other such that the upward deflection of the second plane with respect to the first plane is about from 20 to 40 degrees; and
   (f) the first plane consists of (i) a curved section forming a portion of the outline edge adapted to situate the cuff on the bridge of the nose and (ii) the first vertex which forms a straight line about 40 to 65 mm.

2. The mask of claim 1 wherein the plan view height of the first plane is about 15 to 35 mm with respect to the line defined by the intersection of the first plane with the longitudinal medial line plane.

3. The mask of claim 1 wherein the plan view height of the second plane is about 15 to 30 mm with respect to the line defined by the intersection of the second plane with the longitudinal medial line plane.

4. The mask of claim 3 wherein the second plane consists of a trapezoidal shape, a second vertex adjacent with a third plane forming a straight line about 50 to 75 mm and the non-parallel sides of the trapezoidal shape substantially comprise the portion of the outline edge adjacent to the portion of the outline edge of the first plane and adapted to situate the cuff within a depression formed by the laterally opposed facial elevations of the nasal and maxilla bones of a mask wearer.

5. The mask of claim 4 wherein the third plane consists of a generally rectangular or trapezoidal shape, a third vertex adjacent with a fourth plane forming a straight line about 50 to 80 mm and the parallel sides of the rectangle or the non-parallel sides of the trapezoidal shape comprise the portion of the outline edge adjacent to the portion of the outline edge of the second plane and adapted to situate the cuff on the cheek of a mask wearer, whereby the second and third plane are in angled relation to each other such that the upward deflection of the third plane with respect to the second plane is about from 35 to 45 degrees.

6. The mask of claim 5 wherein the fourth plane consists of (i) a curved section forming a portion of the outline edge adjacent to the outline edge of the third plane and adapted to situate the cuff on the chin and (ii) the third vertex, whereby the third and fourth plane are in angled relation to each other such that the upward deflection of the third plane with respect to the second plane is about from 1 to 10 degrees.

7. The mask of claim 5 wherein an apical portion of the support shell forms an interior surface comprising an upper plane comprising a trapezoidal shape symmetrical about the longitudinal medial line plane, is substantially parallel to the third plane and is, in an elevation distance normal to the third plane and the upper plane, separated from the third plane by about 32–50 mm, wherein a shorter parallel edge of the trapezoidal shape of the upper plane is, in a plan view of the upper plane, about 2 to 10 mm from an end of the longitudinal medial line at the curved portion of the first plane, whereby the interior surface of the support shell generally extends in an outwardly curved shape from the edges of the upper plane to the lower edge of the support shell.

8. A respirator or anesthesia mask for a normal adult comprising:
   (a) an inflatable cuff;
   (b) a support shell with an interior surface adapted to be directed to the face of a patient;
   (c) cuff attachment means that sealingly interpose between and secure the inflatable cuff to the support shell at a lower edge of the support shell;
   (d) a face directed outline edge adapted to comprise an innermost support edge of the cuff attachment means, where such outline edge is symmetrical about a longitudinal medial line plane of the mask;
   (e) the outline edge forming defining edges of at least two planar shapes perpendicular to the longitudinal medial line plane, a first plane in a nose bridge section and a second plane in a nasal/maxilla section, the first plane and second plane having a first vertex joining them in angled relation to each other such that the upward deflection of the second plane with respect to the first plane is about from 20 to 40 degrees;
   (f) the first plane consists of (i) a curved section forming a portion of the outline edge adapted to situate the cuff on the bridge of the nose and (ii) the first vertex which forms a straight line about 40 to 65 mm;
   (g) the second plane consists of a trapezoidal shape, a second vertex adjacent with an imaginary third plane forming a straight line of about 50 to 75 mm and the non-parallel sides of the trapezoidal shape substantially comprise the portion of the outline edge adjacent to the portion of the outline edge of the first plane and adapted to situate the cuff within a depression formed by the laterally opposed facial elevations of the nasal and maxilla bones of a mask wearer;
   (h) the imaginary third plane is in angled relation to the second plane such that the upward deflection of the third plane with respect to the second plane is about from 35 to 45 degrees; and
   (i) an apical portion of the support shell forms a portion of the interior surface comprising an upper plane comprising a generally trapezoidal shape symmetrical about the longitudinal medial line plane, is substantially parallel to the third plane and is, in an elevation distance normal to the third plane and the upper plane, separated from the third plane by about 32–50 mm, wherein a shorter parallel edge of the trapezoidal shape of the upper plane is, in a plan view of the upper plane, about 2 to 10 mm from an end of the longitudinal medial line at the curved portion of the first plane, whereby the interior surface of the support shell generally extends in an outwardly curved shape from the edges of the upper plane to the lower edge of the support shell.

9. The mask of claim 8 wherein the plan view height of the first plane is about 15 to 35 mm with respect to the line defined by the intersection of the first plane with the longitudinal medial line plane.

10. The mask of claim 8 wherein the plan view height of the second plane is about 15 to 30 mm with respect to the line defined by the intersection of the second plane with the longitudinal medial line plane.

* * * * *